United States Patent [19]

Marsili

[11] Patent Number: 4,551,453

[45] Date of Patent: Nov. 5, 1985

[54] 2-(ω-ALKYLAMINOALKYL)- AND 2-(ω-DIALKYLAMINOALKYL-3-(4-X-BENZYLIDENE)-PHTHALIMIDINES

[75] Inventor: Antonio Marsili, Pedona di Camaiore, Italy

[73] Assignee: Laboratori Baldacci SpA, Pisa, Italy

[21] Appl. No.: 518,848

[22] Filed: Aug. 1, 1983

[30] Foreign Application Priority Data

Jun. 8, 1982 [IT] Italy ............................. 22759 A/82

[51] Int. Cl.$^4$ ................... A61K 31/40; C07D 209/46; C07D 411/06
[52] U.S. Cl. .................................. 514/234; 514/416; 544/144; 548/465; 548/472
[58] Field of Search ............... 542/449, 450; 544/144; 548/465, 472; 514/234, 416

[56] References Cited

U.S. PATENT DOCUMENTS 2,957,872 10/1960 Huebner .............................. 544/144
3,031,458  4/1962 Huebner .............................. 544/144
3,091,568  5/1963 Bub .................................... 544/144

Primary Examiner—Donald G. Daus
Assistant Examiner—William A. Teoli, Jr.
Attorney, Agent, or Firm—Murray, Whisenhunt and Ferguson

[57] ABSTRACT

The 2-(ω-alkylaminoalkyl)- and 2-(ω-dialkylaminoalkyl)-3-(4-X-benzylidene)phthalimidines are useful as local anesthetics. For the preparation, the adduct is formed between the suitable 3-(4-X-benzylidene)phthalide and a substituted amino-alkylamine, the adduct being then reacted with acetic anhydride; the X substituent at the position 4 of the benzylidene group then can be suitably converted according to the requirements.

12 Claims, No Drawings

2-(ω-ALKYLAMINOALKYL)- AND 2-(ω-DIALKYLAMINOALKYL-3-(4-X-BENZYLIDENE)-PHTHALIMIDINES

The present invention relates to 3-arylidenephthalimidine derivatives having general formula:

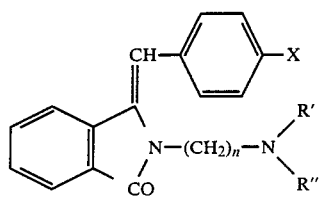

wherein X and R' may be both hydrogen atoms and R" a methyl or ethyl group; or X may represent OH, OCOCH$_3$, OCH$_3$, OCOOC$_2$H$_5$, NO$_2$, NH$_2$, ethyl groups or part of a morpholine or other heterocyclic ring; n may be either 2 or 3.

The novel derivatives according to the present invention find use, both in form of free bases and in form of hydrochlorides, as local anesthetics.

The subject compounds can be prepared according to the invention by heating to 100° C. the proper 3-(4-X-benzylidene)phthalide with β-methylaminoethylamine (or β-ethylaminoethylamine, β-dimethylaminoethylamine, β-dietylaminoethylamine, γ-dimethylamino propylamine, β-(N-morpholinyl)ethylamine, respectively) in a slight excess (about 15%) with respect to the equimolar amount; the crude reaction mixture, containing the adduct between the amine and the 3-(4-X-benzylidene)phthalide is then treated with acetic anhydride at 100° C. and the 3-(4-X-benzylidene)phthalimidine derivatives thus formed are isolated and purified in form of hydrochlorides or free bases.

The X group may be suitably converted depending on the requirements.

The following examples illustrate, without limiting purpose, the preparation of the novel derviatives according to the invention.

In this connection, it is to be noted that, as regards the amines being used, commercially available product are involved. More particularly, 3-benzylidenephthalide, 3-(4-methoxybenzylidene)phthalide and 3-(4-nitrobenzylidene)phthalide are substances disclosed in the literature (R. Weiss, *Organic Sinthesis*, Coll. Vol. 2, 61 (1943); A. Horeau J. Jacques, *Bull.Soc. Chimi. FR* 53 (1943); K/Kodama, *J. Pharm. Soc. Japan*, 63 54 (1943); E. Leupold, *Ber.*, 34, 2829, (1901)), whereas 3-(4-hydroxybenzylidene)phthalide was prepared as described in the example 1.

EXAMPLE 1

15 g of phthalic anhydride, 17 g of 4-hydroxyphenylacetic acid and 0.5 g of freshly molten sodium acetate are charged in a 100 ml flask with a wide neck. The flask is closed with a cork plug having a thermometer extending almost to the bottom and of a bent glass tube, the flask being placed in a sand bed. The mixture is then heated rapidly to 230° C. and then, over 4 hours, to 250° C. The reaction mixture is spontaneously cooled and, upon a 100° C. temperature is reached, treated with ethyl alcohol (200 ml) by refluxing for 30 minutes. After cooling 15 g of 3-(4-hydroxybenzylidene)-phthalide are collected, in form of white needles, having melting point of 262°–264° C.

EXAMPLE 2

51 g of 3-(4-hydroxybenzylidene)-phthalide are suspended in 400 ml of ethyl alcohol and the suspension is added with 25 ml of β-diethylaminoethylamine. The mixture is heated at reflux temperature until a complete solution is obtained (about 1 hour) and then the solvent and the amine excess are evaporated under reduced pressure by means of a rotary evaporator.

The residue is added with 200 ml of acetic anhydride and the mixture is heated to reflux temperature by two hours. The acetic anhydride excess is removed under reduced pressure in a rotary evaporator and the residue is dissolved in 200 ml of ethyl alcohol, previously saturated with hydrogen chloride. By adding 200 ml of ethyl ether and leaving at rest, 55 g of 3-(4-acetoxylbenzylidene)2-(β-diethylaminoethyl)-phthalimidine precipitate, which can be purified by crystallization from ethyl alcohol or from ethylalcohol-ethyl ether. White needles are obtained having m.p. 178°–180° C.

EXAMPLE 3

10 g of the hydrochloride of the preceding example are dissolved in 200 ml of water. The solution is poured in a separating funnel, 200 ml of ethyl ether are added and the mixture is treated with 100 ml of 10% aqueous sodium hydroxide. The mixture is thoroughly shaken, the ether phase is separated and the aqueous phase is extracted again with 100 ml of ethyl ether. The combined ether extracts are dried over anhydrous sodium sulphate, evaporated up to 50 ml volume and the solution is supplemented with 50 ml of hexane. 8.5 g of 2-(β-diethylaminoethyl)-3-precipitate in form of white prisms having m.p. 82°–83° C.

EXAMPLE 4

10 g of 2-(β-diethylaminoethyl)-3-(4-acetoxybenzylidene)-phthalimidine are refluxed over 3 hours with 50 ml of a 10% alcoholic solution of potassium hydroxide. The mixture is then diluted with 50 ml of water and the resulting solution is saturated with carbon dioxide. There are obtained 8.5 g of 2-(β-diethylaminoethyl)-3-(4-hydroxylbenzyliden)phthalimidine which, by crystallization from ethyl alcohol-water, is in form of yellowish plates, with m.p. 135°–137° C.

EXAMPLE 5

4 g of the product of the preceeding example are dissolved in 10 ml of boiling ethyl alcohol and the solution is added with 5 ml of ethyl alcohol previously saturated with hydrogen chloride, and 10 ml of ethyl ether.

After cooling, the resulting precipitate is collected and crystallized from ethyl alcohol-ethyl ether. There are obtained 4 g of 2-(β-diethylaminoethyl)-3-(4-hydroxybenzylidene)-phthalimidine hydrochloride in form of needles, having m.p. 265°–268° C. with composition.

EXAMPLE 6

3 g of the compound of the preceeding example are dissolved in 40 ml of water and the solution is supplemented with 6 ml of 15% aqueous solution of sodium hydroxide. The resulting solution is externally cooled with ice and treated, dropwise and under stirring, with 2 ml of ethyl chloroformate. The mixture is maintained at rest for one hour at room temperature and thereafter the thus formed white precipitate is collected, comprising 2-(β-diethylaminoethyl)-3-(4-ethoxycarbonyloxy benzylidene)phthalimidine. The latter, after drying has a weight of 2.7 g and m.p. 87°–89° C. The product is in form of white prisms.

EXAMPLE 7

By dissolving 2 g of the compound of the preceeding example in 5 ml of ethyl alcohol containing 0.5 ml of concentrated hydrogen chloride and by adding 2 ml of ethyl ether, the 2-(β-diethylaminoethyl)-3-(4-ethoxycarbonyloxy benzylidene)phthalimidine hydrochloride precipitates, which is crystallized from ethyl alcohol-ethyl other. 2 g of product are obtained in form of white prisms with m.p. 116°–118° C.

EXAMPLE 8

1.0 g of 2-(β-diethylaminoethyl)-3-(4-hydroxybenzylidene)phthalimidine are dissolved in 10 ml of acetone. The solution is added with 0.2 g of anhydrous potassium carbonate and 1.0 ml of methyl iodide and the mixture is refluxed for 3 hours. The inorganic phase is separated by filtration, and the residue is evaporated and crystallized from ethyl ether-hexane. There are obtained 0.9 g of 2-(β-diethylaminoethyl)-3-(4-methoxybenzylidene)phthalimidine in form of yellow prisms with m.p. 53°–55° C.

EXAMPLE 9

2-(β-diethylaminoethyl)-3-(4-methoxybenzylidene)phthalimidine hydrochloride is prepared according to the method described in the example 5.

Starting with 0.5 g of the compound described in the example 8, 0.5 g of product are obtained which, after crystallization from ethyl alcohol-ethyl ether, is in form of yellow prisms with m.p. 170°–172° C.

EXAMPLE 10

A suspension of 12.5 g of 3-(4-methoxybenzylidene)phthalide in 50 ml of ethyl alcohol is added with 8 ml of β-dimethylaminoethylamine and the mixture is heated to the reflux temperature until a homogeneous solution is obtained (about one hour). Then the volatile part is removed by evaporating under reduced pressure at 100° C. by means of a rotary evaporator, and the residue is added with 50 ml of acetic anhydride.

After heating the mixture at the refluxing temperature for 2 hours, it is again evaporated at 100° C. under reduced pressure by means of a rotary evaporator and the residue is dissolved in 30 ml of ethyl alcohol saturated with hydrogen chloride. By adding 30 ml of ethyl ether 13 g of 2-(β-dimethylamino ethyl)-3-(4-methoxybenzylidene)phthalimidine hydrochloride precipitate, which are purified by crystallization from acetone or ethyl alcohol-ethyl ether.

There are obtained white prisms with m.p. 223°–225° C.

EXAMPLE 11

By carrying out the reaction under the same conditions of example 8 and by using the same proportions of reactants, but using β-diethylaminoethylamine instead of β-dimethylaminoethylamine, there are obtained 12.5 g of 2(β-diethylaminoethyl)-3-(4-methoxybenzylidene)phthalimidine hydrochloride, in form of yellow prisms with m.p. 170°–172° C.

EXAMPLE 12

By using in the reaction of example 8 α-dimethylaminopropylamine, 15 g of 2-(α-dimethylaminopropyl)-3-(4-methoxybenzyliden)phthalimidine hydrochloride are obtained in form of white prisms with m.p. 206°–208° C.

EXAMPLE 13

By using the reaction of example 8 α-(N-morpholinyl)ethylamine, 13.5 g of 3-(4-methoxybenzylidene)-2-[β-(N-morpholinyl)ethylamino]phthalimidine hydrochloride is obtained as white prisms with m.p. 222°–225° C.

EXAMPLE 14

A suspension of 8.5 g of 3-(4-nitrobenzylidene)phthalide in 65 ml of ethyl alcohol is added with 5.5 ml of β-diethylaminoethylamine and the mixture is heated to the reflux temperature for one hour.

The volatile part is then removed by evaporating under reduced pressure at 100° C. in a rotary evaporator and the residue is added with 20 ml of ethyl alcohol and 5 ml of concentrated hydrogen chloride.

The mixture is thereafter heated to 95° C. for 30 minutes, diluted with 10 ml of water and cooled to 0° C.

There is separated a solid which is collected and crystallized from ethyl alcohol. 8.5 g of 2-(β-diethylaminoethyl)-3-(4-nitrobenzylidene)-phthalimidine hydrochloride are obtained, in form of yellow prisms with m.p. 205°–209° C. with decomposition.

EXAMPLE 15

1.2 g of the product of the preceeding example are dissolved in 150 ml of ethyl alcohol and the solution is added with 0.1 of 5% palladium on carbon. The mixture is stirred under hydrogen atmosphere and at standard conditions until 200 ml of hydrogen were absrobed (about 30 minutes). After filtration, the filtrate is evaporated and the residue is crystallized from ethyl alcholo-ethyl ether. 0.9 g of 2-(β-diethylasminoethyl)3-(4-aminobenzylidene)phthalimidine are obtained in form of yellow prisms with m.p. 188°–190° C. with decomposition.

EXAMPLE 16

A mixture comprising 30 g of 3-benzylidenephthalide, 10 ml of β-methylaminoethylamine and 50 ml of ethyl alcohol is refluxed for one hour.

The resulting solution is evaporated under reduced pressure by means of a rotary evaporator and the residue is refluxed for 30 minutes with 50 ml of acetic anhydride.

The thus obtained residue by further evaporation under reduced pressure is treated with 50 ml of ethyl alchol saturated with hydrogen chloride and refluxed for 3 hours. By adding to the solution 50 ml of ethyl ether, 20 g of 2-(β-methylaminoethyl)-3-benzylidenephthalimidine hydrochloride precipitate which are purified by crystallization from ethyl alcohol-ethyl ether. White needles are obtained with m.p. 253°–255° C.

EXAMPLE 17

By using in the reaction of example 16 β-ethylaminoethylamine instead of β-methylaminoethylamine, and by operating in the same manner, 23 g of 2-(β-ethylaminoethyl)-3-benzylidene-phthalimidine hydrochloride are obtained, in form of white needles with m.p. 260°–263° C.

The compounds of the present invention were subjected to toxicological and pharmacodynamic investigations and experiments. The experimental results of the toxicological tests relating to 3-(4-methoxybenzylidene)-2-(β-diethylaminoethyl)-phthalimide and to 3-(4-acetoxybenzylidne)-2-(β diethylaminoethyl)-phthalimidine hydrochloride are reported hereinafter. For convenience in the following these compounds shall be indicated by the abbreviations AL12 and AL12B respectively.

Lethality and toxicity for single dose

The results are reported in the following table:

| species | AL 12 administration route | LD 50 mg/kg | species | administration route | LIDOCAINE LD 50 mg/kg |
|---|---|---|---|---|---|
| mice | i.v. | 13.5 | mice | i.v. | 32 |
| mice | intramuscolar | 32.5 | | | |
| rat | i.p. | 52.5 | | | |

From the Table it can be noted that the acute toxicity in the mice by i.v. route is about 2.4 (2.37) times higher for AL 12 in comparison with lidocaine.

Since the latter, as it appears from the pharmacodynamic tests is about 4 times less active than AL 12, the therapeutical quotient is favourable for the compound of the invention in the proportion 1.65/1.

Subacute toxicity

It was tested in two stocks of Wistar rats, in three groups each comprising 20 animals, (10 male and 10 female).

One group served as the control; the animals of the other two groups were respectively treated with 10 mg/kg of AL 12 or lidocaine at equivalent molecular dose.

The injections were carried out by intramuscolar route in a point of the thigh for 15 days.

All the animals treated with the active substances (the group administered with lidocaine being also comprised) lost the functionality of the injected leg for about one hour.

All the other functions remained unchanged. Nothing out of the rule was observed at the autoptic examination. The weight of the organs of the treated animals did not differ from that of the control animals.

The food consumption and the diuresis were normal all along the treatment period. The same holds true for the hemocytometric and the hematochemical tests, as carried out at the beginning and at the end of the same period.

Mutagenesis tests

The compound AL 12 was subjected to the tests of genic mutation. All the tests used for such experiments were carried out and precisely:
(a) Ames test using as the substrate a protocariote organism as *Salmonella Typhymurium;*
(b) Test of genic mutation (forwardly) of Schizosaccharomyces Pombe, permitting the evaluation of every mutagenic event capable of varying the functionality of every 5 genes involved in the synthesis of adenine;
(c) DNA recovery test, i.e. test of the non programmed synthesis of recovery DNA on the cellular line Hela of human fibroplasts.

In all three tests AL 12 was unable to induce mutations up to the concentration of 5 ml, whereas the substances used as the active controls to confirm the validity of the method caused the expected mutations to take place.

In order to shown the potential toxicity of the compound AL 12 B a toxicological study was programmed which either for the duration of the administration period (60 days), and for the route of introduction in the organism (intramuscular) and for the variety of used dosages (5-10-20 mg/kg) was surely suitable to indicate the possible toxicity of the substance.

It is pointed out that the lowest dose used in the test is already about 5 to 10 times higher than the single therapeutical dose, possibly used by infiltration in the human being. Male and female rats, having respectively a body weight of about 90 and 65 g, were divided in groups of 6-9 animals of the same sex and stalled in 2 to 3 animals per cage with water and food ad libitum.

The environment conditions were maintained constant at 24° C., moisture at night-day cycle.

The drug in apirogenic sterile solution was daily injected by intramuscolar route. At the end of the treatment the animals were anesthetized for the blood removal for the hematochemical and hematological examinations. The animals were than sacrificed and the weight of the single fresh organs was carefully recorded. The hematochemical parameters which were taken into consideration were the following: glycemia, uricemia, alkaline phosphatase (ALP) malate dehydrogenase (MDH), acetylcholinesterase (CHE), SGPT, SGOT, L-y-glutamyltransferase (Y.G.T.), ornitincarbonyltransferase (O.C.T.), triocylglycerolacylhydrolase (Lipase), isocitratedehydrogenase (ICDH), sorbitole dehydrogenase (SDH), hydroxybutyrate dehydrogenase (HCDH), lactic dehydrogenase (LDHP), lecithin arylamidasi (LAP), sodiemia, potassiemia, chloridemia, magnesiemia, calcemia, total tryglicerides, albumins, globulins, A/G total proteins, total cholesterole, amylasemia, creatininemia. Some hematological parameters were furthermore measured: red corpuscles, platelets, white corpusles, leucocitary form, hemoglobine.

The urinary parameters taken into consideration were, besides the 24 hour volume, azotemia, creatininuria, amylasuria, uricuria, calciuria, chlorides, sodium and potassium.

For the statistical evaluations of the weight of the fresh organs the analysis of the covariations was effected in order to eliminate the possible influences of the body weight onto the organ weight.

Thus the possible significant variation are undoubtedtly to be attributed to the action of the drug.

The hematological and hematochemical parameters were statistically balanced by means of the variancy analysis by taking into consideration all the gropus and the Student "t" amongst the single treated groups and the control group.

The homogeneity of the leucocitary form was investigated by the $\chi^2$ test.

The body weight growth of the animals, both male and female, treated with AL 12B was found comparable with that of the control animals and, altough in the male rats appeared tendentially reduced with the higher dosages (10–20 mg/kg), by the statistical analysis their significance was excluded.

Amongst all the investigated parameters, none appeared to be modified by the treatment with AL 12B at the dose of 5 mg/kg.

Some statiscally significant modifications were instead found in the animals treated with the dose of 10 mg/kg: as regards the weight of the organs only a slight increase of the spleen weight in the male animals was found, it however being not found in the female animals; amongst the hematochemical parameters there was found a reduction of glycemia and of albumins in the male animals accompanied by a slight increase of ALP, found also in the female animals. In the latter, furthermore, an increase of HBDG, LDH-P and of globulins was found.

None of the hematological parameters was modified in any of the male and female animals, whereas amongst the urinary parameters of the male animals the amylasuria and urinary chloride appeared to be reduced. In the female animals no alteration might be appreciated.

At the dose of 20 mg/kg only the weight of the suprarenal glands and of the spleen in the male rats was increased. In the female animals no alteriation might be appreciated. From the examination of the data obtained through these experiments it appears that the AL 12B compound is not particularly toxic, since the first toxic alterations of the examined parameters appears at dosages largely higher (10 times) than the single dose useful in the human being. Furthermore it is to be noted that, owing to the type of use of the anesthetic, it is unimaginable that high dosages are repeated for such a long time to induce the same effect as those found in the experimental work. On the other side it is worth to point out that the modifications ns of the parameters, apart from the spleen swelling and the ALP increase, were not present in both sexes and sometimes were contradictory depending on the sex (see albumin and globulin).

Moreover none of the observed modifications, was shown to be dose-dependent, since most of them were reduced upon the dose was increased.

As regards the pharmacodynamic tests, they were carried out on the following compounds:
(a) 3-benzylidene-2-(γ-dimethylaminopropyl)-phthalimidine hydrochloride (indicated by the abbreviation AL 5)
(b) 3-(4-methoxybenzylidene)-2-(β-diethylaminoetyl)phthalimidine hydrochloride (AL 12)
(c) 3-(4-acetylxybenzylidine)-2-(β-diethylaminoethyl)phthalimidine hydrochloride (AL12B)

The local anesthetic power of these compounds was tested in comparison with procaine, xylocaine and tetracaine.

Test of the rabbit cornea

There were used amounts of AL 12 of 0.25-0.-50-1.0% in comparison with amounts of 1% and 2% of xylocaine.

The complete anesthesy induced by 0.25% AL 12 has a duration of 30 minutes and is therefore slightly lower than that induced by xylocaine at a 4 times higher concentration.

The duration of the complete anesthesy induced by 0.50% AL 12 is more than 90 minutes whereas that induced by 2% xylocaine has a duration of 60 minutes only. At these concentrations, consequently, the anesthetic power of AL 12 is higher that that of xylocaine at a 4 times higher dose.

Test on the sciatic nerve of frog

There was assessed the concentration of the tested substances (AL 12, AL 12 B and AL 5) capable of inhibiting or reducing the action potential of the sciatic nerve of edible frog after removal of a lenght of perinerium.

The stimulating device was sending maximum pulses of 0.1 msec of duration.

The reductions of the action potential after application of the substances were indicated as percentages of the initial action potential.

The comparison substance was procaine at the following concentrations: 0.4–0.6 and 0.8M The $ED_{50}$ of AL 12 B corresponds to a 0.08M concentration in comparison with 0.4M concentration of procaine.

AL 12 B is thus at least 8.5 times more powerful than procaine.

From the other comparisons it is found that AL 12 is about 11.5 times and AL 5 about 5 times more powerful than the comparison substance.

Since the lidocaine, as unanimously stated in the literature, has a local anesthetic activity which is about 2.2 times higher than that of procaine, it can be desumed that AL 12 B is about 4 times more active than lidocaine and AL 12 is about 5–6 times more active of the same.

Test of inhibition of the action potential of the vagal nerve of chicken

For these tests two investigation parameters were selected:
(a) increase of the stimulating threshold necessary to induce the appearance of the action potential;
(b) inhibition of the potential width as induced by the supra maximum stimulation. AL 12 and AL 12 B were compared with the tetracaine.

The effects of the tested compounds are almost perfectly superimposable to those of tetracaine used at the same molar concentrations.

The $ED_{50}$ was calculated for AL 12 with respect to parameter (a) (increase of the stimulation threshold) and resulted to be about $6.5 \times 10^{-5}M$ as for tetracaine. The ED 50 of AL 12 in the inhibition of the width of the action potential for stimulations higher than the maximum was found to be $8 \times 10^{-9}M$ and it corresponds too to that of tetracaine.

I claim:

1. A method of inducing local anesthesia in a patient comprising applying at the locus to be anesthetized a local anesthetic effective amount of a compound having the formula

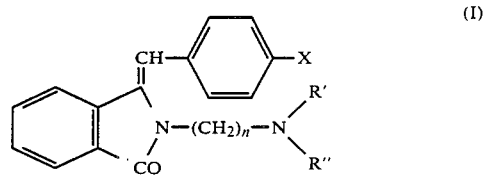
(I)

wherein X and R' are both hydrogen atoms and R" is a methyl or ethyl group; or R' and R' are both methyl or ethyl groups, or R' and R" together with the nitrogen atom to which they are attached may be a morpholino group, and X represents OH, $OCOCH_3$, $OCH_3$, $OCOOC_2H_5$, $NO_2$ or $NH_2$; and n may be either 2 or 3; or the hydrochloride thereof.

2. The method according to claim 1, wherein said compound is 2-(β-diethylaminoethyl)-3-(4-acetoxybenzylidene)phthalimidine or the hydrochloride thereof.

3. The method according to claim 1 wherein said compound is 2-(β-diethylaminoethyl)-3-(4-hydroxybenzylidene)phthalimidine or the hydrochloride thereof.

4. The method according to claim 1, wherein said compound is 2-(β-diethylaminoethyl)-3-(4-ethoxycarbonyloxybenzylidene)phthalimidine or the hydrochloride thereof.

5. The method according to claim 1, wherein said compound is 2-(β-diethylaminoethyl)-3-(4-methoxybenzylidene)phthalimidine or the hydrochloride thereof.

6. The method according to claim 1, wherein said compound is 2-(β-methylaminoethyl)-3-benzylidene phthalimidine or the hydrochloride thereof.

7. The method according to claim 1, wherein said compound is 2-(β-ethylaminoethyl)-3-benzylidene phthalimidine or the hydrochloride thereof.

8. The method according to claim 1, wherein said compound is 2-(β-dimethylaminoethyl)-3-(4-methoxybenzylidine)phthalimidine or the hydrochloride thereof.

9. The method according to claim 1, wherein said compound is 2-(β-diethylaminoethyl)-3-(4-nitrobenzylidene)phthalimidine or the hydrochloride thereof.

10. The method according to claim 1, wherein said compound is 2-(β-diethylaminoethyl)-3-(4-aminobenzylidene)phthalimidine or the hydrochloride thereof.

11. The method according to claim 1, wherein said compound is 2-(γ-dimethylaminopropyl)-3-(4-methoxybenzylidene)-phthalimidine or the hydrochloride thereof.

12. The method according to claim 1, wherein said compound is 2-[β-(N-morpholinyl)ethyl]-3-(4-methoxybenzylidene)-phthalimidine or the hydrochloride thereof.

* * * * *